(12) United States Patent
Hirsch

(10) Patent No.: US 8,399,397 B2
(45) Date of Patent: *Mar. 19, 2013

(54) ARTICLES AND COMPOSITIONS FOR ENHANCING SPORTS SCORES

(76) Inventor: Alan R. Hirsch, Riverwoods, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/951,250

(22) Filed: Nov. 22, 2010

(65) Prior Publication Data

US 2011/0064672 A1 Mar. 17, 2011

Related U.S. Application Data

(62) Division of application No. 11/617,039, filed on Dec. 28, 2006, now Pat. No. 7,838,486.

(60) Provisional application No. 60/754,499, filed on Dec. 28, 2005.

(51) Int. Cl.
| | | |
|---|---|---|
| A61K 8/00 | (2006.01) | |
| A61K 8/18 | (2006.01) | |
| A61Q 13/00 | (2006.01) | |
| C11B 9/00 | (2006.01) | |
| C11B 9/02 | (2006.01) | |

(52) U.S. Cl. ............................................. 512/1; 512/5
(58) Field of Classification Search ....................... 512/1
See application file for complete search history.

(56) References Cited

U.S. PATENT DOCUMENTS

| | | |
|---|---|---|
| 5,380,765 A | 1/1995 | Hirsch |
| 5,455,043 A | 10/1995 | Fischel-Ghodsian |
| 5,492,934 A | 2/1996 | Hirsch |
| 5,759,521 A | 6/1998 | Hirsch |
| 5,885,614 A | 3/1999 | Hirsch |
| 5,904,916 A | 5/1999 | Hirsch |
| 5,949,522 A | 9/1999 | Manne |
| 6,019,101 A | 2/2000 | Cotner et al. |
| 6,089,227 A | 7/2000 | Nilsson |
| 6,106,837 A | 8/2000 | Hirsch |
| 6,769,428 B2 | 8/2004 | Cronk et al. |
| 6,803,987 B2 | 10/2004 | Manne |
| 6,866,041 B2 | 3/2005 | Hardy, Jr. et al. |
| 7,067,162 B1 | 6/2006 | Hirsch |
| 7,108,872 B1 | 9/2006 | Hirsch |
| 7,838,486 B2 | 11/2010 | Hirsch |
| 2002/0189608 A1 | 12/2002 | Raudenbush |
| 2003/0147938 A1 | 8/2003 | Hirsch |
| 2004/0137086 A1 | 7/2004 | Hirsch |
| 2006/0057232 A1 | 3/2006 | Hirsch |

OTHER PUBLICATIONS

"A Pleasant Scent Can Lead to a Good Night's Sleep," Sense of Smell Institute, http://www.senseofsmell.org/feature/sleep/index.pdf (2009).
Amoore et al., "Proposal for a Unifying Scale to Express Olfactory Thresholds and Odor Levels: The Decismel Scale," in Proceedings of the 1988 Air Pollution Control Association Annual Meeting, Paper No. 78.5 (21 pp.), Air and Waste ManagementAssociation.
Amoore, et al., "Odor as an aid to chemical safety: odor thresholds compared with threshold limit values and volatilities for 214 industrial chemicals in air and water dilution," Journal of Applied Toxicology, vol. 3, No. 6, 1983.
Amoore, et al., "Practical Test Kits for Quantitatively Evaluating the Sense of Smell," Rhinology, vol. 21, 1983 (pp. 49-54).
Bowlfit test document 2004, (Apr. 16, 2004 [retrieved form the internet on Apr. 14, 2009<URL: http://web.archive.org/web/20040416033348/http://webpages.charter.net/bow- lfit/asian/2000/9.pdf.
Boyce, et al., "The Effects of Self-Efficacy and Goal Setting on Bowling Performance," Journal of Teaching in Physical Education (JTPE), vol. 16, No. 3, Apr. 1997.
Doty et al., "The Olfactory and Cognitive Deficits of Parkinson's Disease: Evidence for Independence" American Neurology Assocation, vol. 25, 1989 (pp. 166-171).
Doty, Richard L., Ph. D., The Smell Identification Test: Administration Manual 1983: 13-14, Philadelphia: Sensonics, Inc. (1983).
Edwards (Bowling Digest, Aug. 2000, retrieved from internet on Feb. 11, 2009, URL: http://findarticles.com/p/articles/mi.sub.--m0FCK/is.sub.--3.sub.--18/ai.- sub.--63652458 pp. 1-2).
Gent et al., Taste and Smell Measurement in a Clinical Setting, in a Clinical Measurement of Taste and Smell, pp. 107-117, H.L. Meiselman et al. (eds.), 602 pp., MacMillan, N.Y. (1986).
Healthcare International, "Peak Performance Sports Inhaler" (2005)—Main page at http://www.sportsinhaler.com (2 pgs.)—"Product Overview" at http://sportsinhaler.com/productoverview.htm (1 pg.)—"Documented Test Results" athttp://www.sportsinhaler.com/d.
Healthcare International, Peak Performance Sports Inhaler, "The Role of Peppermint Odor Administration on Nasal Dilation and Lung Capacity, Brief Report", 2005 (2 pp.), at http://www.sportsinhaler.com/article.sub.--2htm.
Healthcare International, News Update & Articles, University Research Leads to World's First 100% All Natural Athletic Enhancer—Peak Performance TM Sports Inhaler TM, 2005 (2pp.) at http://www.sportsinhaler.com/newsupdates.htm.
Hirsch et al., Chemical Senses vol. 17, No. 5, 1992 (pp. 642, 642-3, 643, 643-4).
Hirsch, et al., "Validation of the Chicago Smell Test (CST) in Subjective Normosmic Neurologic Patients," Chemical Senses, vol. 18, No. 5, Oct. 1993.
Ilmberger, et al., "The Influence of Essential Oils on Human Attention, 1: Alertness", Chemical Senses, vol. 26, No. 3, Apr. 2001 (pp. 239-245).
Koss et al., "Olfactory Detection and Identification Performance and Dissociated in Early Alzheimer's Disease", Neurology, vol. 38, 1988 (pp. 1228-1232).
MacKenzie, Cheryl, "Peppermint Odor and Athletic Performance: An Ergogenic Aid or An Expectancy Effect?", Powerpoint Presentation, 9 pp., (c. 2005), http://ergo.human.cornell.edu/Grads/CMMDefense%20Presentation%206.15.pdf.
Raudenbush, Positive Effects of Odorant Administration on Humans A review, Sense of Smell, Nov. 18, 2005, pp. 1-29.

(Continued)

*Primary Examiner* — Savitha Rao
(74) *Attorney, Agent, or Firm* — Whyte Hirschboeck Dudek SC

(57) ABSTRACT

Methods and compositions for enhancing the score of an individual in a sport activity are disclosed.

19 Claims, No Drawings

OTHER PUBLICATIONS

Raudenbush, Bryan, "The Effects of Peppermint on Enhancing Mental Performance and Cognitive Functioning, Pain Threshold and Tolerance, Digestion and Digestive Processes, and Athletic Performance," Wheeling Jesuit University Dept. Psychology, prepared for the Sense of Smell Institute, The Research & Education Division of The Fragrance Foundation (2004) at http://www.senseofsmell.org/papers/B_Raudenbush_peppermint.pdf.

Raudenbush, et al., "Enhancing athletic performance through the administration of peppermint odor," Brief Report, J. Sport & Exercise Psychology, vol. 23, No. 156, 2001, (4 pp.), at http://www.sportsinhaler.com/article.sub.--1.

Raudenbush, et al., Enhancing Athletic Performance Through the Administration of Peppermint Odor,: Journal of Sport and Exercise Psychology (JSEP), vol. 23, No. 2, Jun. 2001.

Schiffman et al., "Effect of pleasant odors on mood of males at midlife: Comparison of African-American and European-American Men," Brain Research Bulletin, vol. 36, No. 1, 1995 (pp. 31-37).

Strickland, Robert H., "Bowling: Steps to Success (Steps to Success Activity Series)," Human Kinetics Publishers, Illinois 1996 (p. 1-162).

White, Theresa L., Ph.D., "Aroma-Chology Benefits to Health and Well-Being Scent, Physical Appearance Skin Care," A Sense of Smell Institute White Paper, Sense of Smell Institute, Apr. 2002.

Yagyu T, abstract, Integrative Psychiatr., vol. 10, No. 2, 1994 pp. 62-67).

ARTICLES AND COMPOSITIONS FOR ENHANCING SPORTS SCORES

CROSS REFERENCE TO RELATED APPLICATION

This application is a divisional application of U.S. Ser. No. 11/617,039, filed on Dec. 28, 2006, now U.S. Pat. No. 7,838,486, which claims priority under 35 U.S.C. §119(e) to Provisional Patent Application Ser. No. 60/754,499, filed on Dec. 28, 2005, the entire disclosure of which is hereby incorporated by reference.

FIELD OF THE INVENTION

The present invention relates to improving an individual's score in the performance of a sport by the administration of odorants to the individual.

BACKGROUND OF THE INVENTION

The sport of bowling has existed for over 7,000 years, having been discovered in Egyptian ruins in about 5200 BC. Its popularity has persisted over the years and millions of Americans bowl each year.

While typically considered to be a recreational sport, bowling has evolved to be part of the current competitive experience. As such, minor variations in bowling score can have substantial impact on outcome. Factors that can influence performance include underlying physical capacity, skill, past learned techniques, hand-eye coordination, degree of alertness, affective state, motivation, self-efficacy, and accuracy in predicting vector analysis concurrent with physical placement of these vectors (Boyce et al., *J. Teaching in Physical Education* 16:312-323 (1997)). In addition, the physical surroundings and ambient environment of a bowler is typically a turbulent sensory invasion: a cacophony of sounds from fellow bowlers and pins falling, a kaleidoscopic image of bowlers blurring the peripheral visual field, and an assault on gestation and olfaction by beer and pizza, superimposed upon by the aroma of stale cigarettes and old bowling shoes. Scientific studies of the effect of these factors on the performance of bowlers is sparse.

Ambient aromas have been demonstrated to impact strength, leisure time activities, and cognitive tests involving precise hand-eye coordination (Raudenbush et al., *J. Sport and Exercise Psychology* 23: 156-160 (2001)). Certain odors have been shown to influence perception on different sensory spheres including perception of age, weight, and external space.

It would be useful to provide a means of enhancing an individual's performance in a sport activity that is non-invasive, convenient, safe, and easy to administer.

DESCRIPTION OF THE INVENTION

The present invention relates to methods of using odorants to enhance an individual's score in the performance of a sport-related activity by the administration of a composition comprising an odorant or mixture of odorants for sniffing and inhalation by an individual into the nasal passageway. In particular, the method involves delivering an effective amount or concentration of an odorant or mixture of odorants to an individual for continuously inhaling during the performance of a sport to enhance the individual's performance of the sport activity by an improved score compared to a base score by the individual when the sport activity is performed without inhalation of the odorant.

In an exemplary embodiment of the method, a composition is administered to an individual to inhale while bowling that comprises a jasmine odorant as the primary or dominant odor (aroma) of the composition to increase the bowling score of the individual compared the score achieved by the individual without inhaling the jasmine odorant composition by a statistically significant amount ($p<0.05$).

As used herein, the term "odorant" refers to an odor-causing chemical compound or mixture of compounds that, when delivered in a gaseous or aerosol medium, can stimulate olfactory and/or trigeminal chemoreceptors in the nasal cavity and cause a physiological or psychological response. A hedonically positive odorant or odorant mixture is one to which the individual has a pleasant or positive reaction to its scent. A hedonically negative odorant or odorant mixture is one to which the individual has a repulsive or negative reaction to its scent. A hedonically neutral odorant or odorant mixture is one to which the individual has neither a positive nor negative reaction.

In a preferred embodiment, the subject individual is presented with the composition containing a suprathreshold concentration (e.g., about 25-55 decismel units) of the odorant or odorant mixture that is near but not so high as to become an irritant (trigeminal), which the individual inhales while performing the activity. The level or concentration of the odorant or odorant mixture within the composition and/or mode of administering the composition is sufficient to overcome competing or conflicting ambient odors that may act to nullify its effect.

An odorant is presented at a "suprathreshold" level when the decismel level or concentration of the odorant is beyond that needed to be detected by a normosmic individual. At its irritative level, the odorant quantity is so high and intense that the odorant stimulates predominantly the trigeminal nerve (for pain) rather than the olfactory nerve and, hence, is perceived as noxious or painful. The irritation threshold of the patient is the lowest concentration of the substance that causes immediate stinging or burning sensations in the nose, or stinging or lacrimation of the eye. (See, J. F. Gent, in *Clinical Measurement of Taste and Smell*, pages 107-166, H. L. Meiselman et al. (eds.), 602 pp., MacMillan, N.Y. (1986); R. L. Doty et al., *Ann. Neurol.* 25: 166-171 (1989); E. Koss et al., *Neurology* 38: 1228-1232 (1988); and R. Doty, *The Smell Identification Test: Administration Manual* 1983: 13-14, Philadelphia: Sensonics, Inc. (1983)).

If desired, prior to the administration of the odorant, the subject individual can undergo olfactory testing according to a test such as the University of Pennsylvania Smell Identification Test (UPSIT), a 40-question forced-choice, scratch-and-sniff identification test, and the Chicago Smell Test, a 3-item detection and identification test (R. Doty, The Smell Identification Test: Administration Manual 1983: 13-14, Philadelphia: Sensonics, Inc. (1983); A. R. Hirsch et al., Chemical Senses 18(5): 570-571 (1993); A. R. Hirsch et al., Chemical Senses 17(5): 643 (1992)).

The subject individual can also be evaluated for olfactory capacity (e.g. loss of smell) according to an olfactory threshold test as known and used in the art. Such a test provides a precise magnitude of loss of smell and classifies the individual as normosmic, hyposmic or anosmic, which is useful in assessing the effectiveness of a particular odorant and/or the required concentration of the odorant, preferably a suprathreshold and near but below irritant level, to provide the desired effect according to the method of the invention. According to that test, an odorant substance such as butyl alcohol, phenyl ethyl alcohol, or pyridine, is combined in an odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The individual is presented with the series of dilutions in ascending order, and is asked to compare each dilution step to at least one control stimulus, such as odorless propylene glycol.

In the art, a "normosmic" individual is one who can detect the odor of a substance without irritant sensations when the odorant is presented with the range of its average normal threshold. A "hyposmic" or "microsmic" individual has reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminal nerve function, being able to detect an odorant substance by means of irritant, tingling sensations when it is present at an irritant concentration. A patient who is able to detect pyridine vapor by means of irritant, tingling sensations caused by stimulation of the trigeminal nerve, but who cannot distinguish a pyridine odor at a lower concentration without such sensation, is considered to be anosmic having no olfactory nerve sensitivity.

Ranges of the average normal threshold for various odorant substances can be found in the art, for example, Amoore and O'Neill, "Proposal for Unifying Scale to Express Olfactory Thresholds and Odor Levels: The "Decismel Scale"," in Proceedings of the 1988 Air Pollution control Association Annual Meeting, Paper No. 78.5 (21 pp.), Air and Waste Management Association, Pittsburgh, Pa. (1988); Amoore and Haotala, "Odor as an Aid to Chemical Safety: Odor Thresholds Compared with Threshold Limit Values and Volatiles for 214 Industrial Chemicals in Air and Water Dilution," J. Appl. Toxicology 3(6):272-290 (1983).

A suprathreshold amount is a concentration of the odorant/odorant mixture that is greater than the average normal threshold concentration of the odorant or mixture. The normal threshold concentration can be determined by administering a series of the same concentrations of the odorant/odorant mixture to a control group of at least 25 individuals who do not have a chemosensory dysfunction, and calculating the mean threshold concentration detected by the group of 25 individuals. Another alternative is to refer to the known threshold concentration value for the odorant/odorant mixture that has been established previously and published by J. Amoore et al., *J. Appl. Toxicology*, 3:272 (1983).

Odor thresholds can be expressed on the decismel scale. The decismel scale is constructed by setting the mean threshold concentration of a chemosensory agent detected by the control group of 20 year olds at the "0" value. A decismel is calculated by dividing the concentration of the odorant detected by the patient by the normal threshold concentration (using the published value or empirically determining the value) and then taking the logarithm of the quotient. The logarithm of the quotient is then multiplied by 20 to obtain the decismel value. Decismel values can be positive or negative. A positive decismel value indicates the patient is less sensitive to the odorant, i.e. has a higher threshold detection concentration. A negative decismel value indicates that the patient is more sensitive to the compound, i.e. has a lower threshold detection concentration. An increase in the threshold concentration value over the mean threshold concentration value of 2 fold corresponds to 6 decismels (or ds). Determination of decismel units is known in the art, as addressed, for example, in U.S. Pat. Nos. 5,380,765 and 5,492,934 (Hirsch).

In another aspect, the invention provides compositions containing an effective amount of an odorant or mixture of odorants such that, when inhaled by an individual while performing a sport activity, the score of the individual is substantially improved. Depending on the nature of the sport, this result can be evidenced by an increased score (e.g., bowling) or by a decreased score (e.g., golf) as compared to the individual's score when the activity is performed while not inhaling the odorant composition (i.e., a control). Such an effect can be objectively assessed and measured by the score of a defined parameter (e.g., a defined number of frames in bowling, etc.) when played with and without administration of the odorant composition.

The concentration of the odorant or mixture of odorants is preferably at a suprathreshold concentration and preferably near but not an irritant concentration at a decismel level of about 25-55 decismel units, preferably greater than 25 decismel units, preferably at about 30-55 decismel units.

In an exemplary embodiment, the composition contains an effective amount of a jasmine odorant as the dominant (primary) odor or essence to increase an individual's bowling score (based on a defined number of frames) by about 25-30% when directly and continuously inhaled by the individual while performing the activity, compared to the individual's bowling score without inhaling the jasmine odorant composition.

The odorant or odorant mixture is provided as a formulated composition of a single essential odorant or a blend (mixture) of the essential odorants to cause the desired effect, and eliminates odorants that compete with or mask the effective odorant(s). The odorant or odorant blend composition can be administered in combination with an odorless carrier such as mineral oil or water, and odorless additives such as preservatives and the like. The odorant composition can be formulated with a viscosity effective to allow for aerosolization or to provide a thick gel or cream.

A preferred odorant composition is a formulation that essentially comprises a jasmine odorant and eliminates odorants that compete with the jasmine odorant accords or notes to provide a full effect on the individual inhaling the odorant composition. A jasmine odorant, and other odorants for use in the present methods, are commercially available as a liquid, essential oil, extract, or other form from a variety of sources, including, for example, Energy Essentials, AromaTech, Inc. (Somerville, N.J.), Florasynth, Inc. (Teterboro, N.J.), International Flavors and Fragrances, Inc. (IFF; New York, N.Y.), among others.

In one embodiment, the composition can consist essentially of a suprathreshold and non-irritant concentration of one or more odorants such that, when inhaled by an individual, the composition is effective to improve a score of the individual in a sport activity by a statistically significant amount compared to the individual's score upon performing said sport activity without inhalation of the composition. For example, the composition can consist essentially of a jasmine odorant in a carrier such that, when inhaled by an individual, the composition is effective to increase the individual's bowling score of a set number of frames by a statistically significant amount compared to the individual's bowling score for the same number of frames without inhaling the composition. In another example, the composition can be composed of a mixture of odorants in a carrier, including a suprathreshold and non-irritant concentration of a jasmine odorant in combination with a less than suprathreshold concentration of one or more odorants that complement and do not mask the jasmine odorant, such that, when inhaled by an individual, the composition is effective to improve a score of the individual in a sport activity by a statistically significant amount.

The odorant composition is preferably formulated as a liquid solution or a spray, but can also be provided in the form of a cream, lotion, or other consistency, and can be contained within a liquid pump device, aerosol or non-aerosol spray device, lidded container, a blister pack, or other suitable vessel such as those known and used in the art. The odorant composition can also be contained in a solid form within a capped vessel. It is preferred that the odorant composition is provided in a portable dispenser that is easily transportable and readily accessible.

In conducting the method of the invention, the odorant composition is administered for direct and continuous inhalation by the subject individual during performance of a sport activity. Such administration can be achieved, for example, by applying an effective amount of the odorant composition in an effective concentration directly to the face of the individual below the nostrils, or to a cloth or paper material such as a mask (e.g., a surgical mask, dust-type mask, earloop face mask, and the like) that is then secured over the nostrils of the subject individual.

In another embodiment, the composition can be administered by means of a flexible laminate material (e.g., patch) sized to fit beneath the nose that incorporates the odorant composition and has a pressure-sensitive adhesive layer (covered by a release layer) that allows the material to adhere to skin and which is positioned under the nostrils of the individual, as described, for example in U.S. Pat. No. 6,769,428 (Cronk).

In yet another embodiment, the odorant composition can be administered through the use of a portable delivery device operable to provide continuous delivery of a vaporous emission of the odorant composition through cannulla (tubes) inserted into the nostrils of the individual as described, for example, in U.S. Pat. No. 6,803,987 (Manne). Other delivery systems can be used for delivery of the odorant composition to the individual.

Odorants or odorant mixtures can be readily screened and assessed for effectiveness in enhancing performance in a sport or sport related activity according to the invention. For example, a composition containing an odorant or mixture of odorants can be administered to an individual for inhalation to evaluate its effect on modifying a score of a sport activity such as bowling, for example, which can be manifested by an increased bowling score compared to the score achieved when the activity is performed without inhaling the odorant composition. Optionally, the individual can be questioned as to a positive or negative reaction to the pleasantness of the scent to assess the hedonics of the odorant composition.

An exemplary method of screening a composition formulated with an odorant or a mixture of odorants for effectively altering an individual's sport score or performance can comprise the steps of:
a) having an individual perform a sport activity (for example, bowling a predetermined number of frames) without inhalation of the target odorant composition and tallying the score ("control score");
b) having the individual re-perform the sport activity from step a) while continuously inhaling a suprathreshold but non-irritant concentration of a composition consisting essentially of the test odorant or odorants, and tallying the score to provide a "test score";
c) comparing the control score to the test score to determine the statistical significance between the two scores; and
e) eliminating the odorant or odorant mixture as being ineffective to enhance performance of the individual in the sport activity if not statistically significant ($p<0.05$).

The screening test as well as the method of the invention can include other steps such as having the inhaling individual identify the composition as hedonically positive, neutral or negative, and testing olfactory ability and/or olfactory capacity of the individual, among other olfactory tests known and used in the art.

According to the invention, a composition comprising the odorant or odorant mixture is continuously dispensed as a vaporous emission to the nostrils of an individual for inhalation of a concentration effective to enhance the individual's score in a sport activity, with bowling being an exemplary activity using a jasmine-based composition. Such an effect can be assessed and measured objectively by comparing the sport score achieved with and without the administration of the odorant composition.

The odorant composition can be packaged as part of an article of manufacture, or kit. In one embodiment, the article of manufacture can comprise a container of an odorant composition or, packaged together, a container of a first odorant and a container of a second odorant (etc.) for combining together to form the odorant composition. The odorant composition comprises an odorant or mixture of odorants in a suprathreshold and but non-irritant concentration, and preferably near a non-irritant concentration, effective to substantially enhance an individual's sports score when administered according to the method of the invention.

In a preferred embodiment, the composition consists essentially of a jasmine odorant. For example, the article of manufacture can comprise a container of an odorant composition consisting essentially of a jasmine odorant, or of one or more odorants of which a jasmine odorant is the dominant odor or essence, and a device for use in delivery of the composition to a subject individual during the performance of the sport activity, for example, a mask for placement over the nose of the individual, a device for applying the composition directly to the skin under the nostrils of the individual, among others.

The kit can further include one or more elements for testing the individual, that can be separately packaged, including a device for administering odorant(s) for testing olfactory ability of the individual (e.g., UPSIT), and/or a device for administering a series of odorants for testing olfactory threshold of the individual (e.g., pyridine dilution series).

The article of manufacture can further comprise written or other format of instructions (e.g., C.D., video, cassette tapes, etc.) for use of the odorant composition for enhancing sport performance in a method according to the invention, including, but not limited to increasing an individual's bowling score. In another embodiment, the article of manufacture can comprise packaging material and an odorant composition according to the invention contained within the packaging material, wherein the packaging material comprises a label that indicates that the odorant composition can be used for enhancing sport performance and/or improve a sports score. The article of manufacture can also include an odorant composition and instructions for testing olfactory threshold according methods known in the art. The parts of the article of manufacturing can be contained or separately packaged within a packaging material, such as a box, bag, pouch, and the like.

The invention will be further described by reference to the following detailed example. This example is not meant to limit the scope of the invention that has been set forth in the foregoing description. Variation within the concepts of the invention is apparent to those skilled in the art. The disclosures of the cited references throughout the application are incorporated by reference herein.

EXAMPLE

Methods. Twenty subjects, in a randomized fashion, bowled one frame (10 pins) while wearing a blank surgical mask (control, Aroma #1) and one frame while wearing a mask impregnated with a jasmine aroma (odorant) (Aroma #2). The individuals also rated the hedonics of the mask impregnated with the jasmine odorant. The jasmine odorant was from International Flavors & Fragrances, Inc., Hazlet, N.J.

The subjects were handed a sheet of paper to fill out as follows:

---

Name:
Age:
Aroma #1
Bowling First Ball: _____ (# of pins)
Bowling Second Ball: _____ (# of pins)
On Scale of 1-10, with 10 being a "very nice smell", 5 being "neutral", and 0 being "don't like smell at all", rate aroma: _____
Aroma #2
Bowling First Ball: _____ (# of pins)
Bowling Second Ball: _____ (# of pins)
On Scale of 1-10, with 10 being a "very nice smell", 5 being "neutral", and 0 being "don't like smell at all", rate aroma: _____

Results. The results are shown in the following table.

The "Rating" category presents the individual's rating of the hedonics of the blank (control) mask and the odorant mask on a scale of 1-10, in which a rating of five (5) indicated a neutral hedonic, a rating of greater than five (>5) indicated a positive hedonic, a rating of less than five (<5) indicated a negative hedonic.

| | | Aroma #1 | | | Aroma #2 | | |
|---|---|---|---|---|---|---|---|
| Subject Number | Age | $1^{st}$ Ball (# pins) | $2^{nd}$ Ball (# pins) | Rating (hedonics) | $1^{st}$ Ball (# pins) | $2^{nd}$ Ball (# pins) | Rating (hedonics) |
| 1 | 17 | 3 | 5 | 5 | 8 | 2 | 10 |
| 2 | 15 | 1 | 2 | 6 | 6 | 4 | 3 |
| 3 | 14 | 10 | 0 | 5 | 10 | 0 | 8 |
| 4 | 16 | 3 | 4 | 7 | 0 | 8 | 3 |
| 5 | 16 | 0 | 1 | 5 | 0 | 2 | 2 |
| 6 | 15 | 0 | 5 | 5 | 1 | 9 | 6 |
| 7 | 16 | 7 | 1 | 6 | 1 | 2 | 8 |
| 8 | 16 | 5 | 2 | 5 | 9 | 1 | 6 |
| 9 | 17 | 8 | 0 | 5 | 9 | 1 | 8 |
| 10 | 17 | 4 | 2 | 5 | 6 | 3 | 7 |
| 11 | 16 | 2 | 3 | 7 | 3 | 4 | 8 |
| 12 | 17 | 1 | 4 | 4 | 2 | 6 | 5 |
| 13 | 15 | 0 | 7 | 5 | 3 | 4 | 3 |
| 14 | 17 | 9 | 0 | 5 | 1 | 9 | 4 |
| 15 | 16 | 1 | 6 | 6 | 4 | 3 | 8 |
| 16 | 17 | 6 | 4 | 5 | 5 | 5 | 8 |
| 17 | 17 | 6 | 1 | 5 | 10 | 0 | 2 |
| 18 | 16 | 3 | 2 | 6 | 2 | 5 | 7 |
| 19 | 16 | 4 | 1 | 4 | 5 | 5 | 6 |
| 20 | 16 | 8 | 1 | 3 | 7 | 2 | 6 |
| Totals | | 81 | 51 | | 92 | 75 | |
| n = 20 | | | 132 | | | 167 | |
| Totals | | 65 | 47 | | 77 | 70 | |
| n = 18 | | | 112 | | | 147 | |
| Totals | | 62 | 36 | | 72 | 78 | |
| n = 14 | | | 98 | | | 120 | |

The Table below summarizes the results of the bowling scores. It is noted that test subject #3 had two strikes and a hedonic rating of the jasmine odorant $\geq 5$, and test subject #17 had one strike and a hedonic rating of <5.

| | Mean ± SD | | | |
|---|---|---|---|---|
| | Total No. of Pins: | | Difference Score | |
| Sample | Blank Mask (Control) | Scented Mask | (Scented minus Control) | Paired T-test t-score (p-value) |
| n = 20 (full sample) | 6.60 ± 2.28 | 8.35 ± 2.35 | +1.75 ± 2.49 | +3.14 (p = .0053) |
| n = 19 (eliminate #3) | 6.42 ± 2.19 | 8.26 ± 2.38 | +1.84 ± 2.52 | +3.18 (p = .0051) |
| n = 18 (eliminate #3 & #17) | 6.39 ± 2.25 | 8.17 ± 2.41 | +1.78 ± 2.58 | +2.92 (p = .0095) |
| n = 14 (hedonic rating $\geq 5$) | 7.00 ± 1.88 | 8.57 ± 2.03 | +1.57 ± 2.53 | +2.32 (p = .0372) |
| n = 13 (hedonic rating $\geq 5$, and eliminate #3) | 6.77 ± 1.74 | 8.46 ± 2.07 | +1.69 ± 2.59 | +2.35 (p = .0366) |

Discussion. With the total group of twenty subjects (n=20), the average score when wearing the blank (control) mask was 6.60 pins per frame, whereas the average score when wearing the jasmine odorant mask was 8.35 pins per frame. The results were statistically significant (p<0.05).

Upon eliminating a ceiling effect (i.e., a score of 10 pins per frame on the best ball for subjects #3 and #17, or n=2), of the eighteen remaining subjects (n=18), the average score when wearing the blank (control) mask was an average of 6.39 pins per frame, and when wearing the jasmine mask was an average of 8.17 pins per frame.

A subdivision of the group to those subjects having less than 10 pins per frame on the best ball and who rated the jasmine odorant/aroma as being neutral or better (n=14), had a total score of 7.0 pins per frame with the blank mask, and 8.6 pins per frame with the mask with the jasmine odorant.

The results also demonstrated that the hedonics of the jasmine odorant did not have a significant effect on the bowling scores of the subject individuals.

Conclusion. Inhalation of a jasmine odorant had a statistically significant effect on improving bowling scores and performance of the tested individuals.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents. The disclosures of the cited patents, applications, and other references throughout the application are incorporated by reference herein.

What is claimed is:

1. An article, comprising, packaged together:
   a container of a composition comprising a jasmine odorant as a dominant odor at a suprathreshold but non-irritant concentration being at about 25-55 decismel units and greater than an average normal threshold concentration of the jasmine odorant, the composition effective upon inhalation to improve an individual's score in a bowling activity of a set number of frames by a statistically significant amount compared to a control score determined by the individual's score of said set number of frames without inhalation of the composition; and
   instructions for administering the composition to an individual by inhalation during performance of the bowling activity and assessing the effectiveness of the composition.

2. The article of claim 1, wherein the container is selected from a blister pack, a liquid pump, a spray device, a lidded container, a capped vessel, and an adherent patch for applying to skin of the individual.

3. The article of claim 1, wherein the composition is in the form of a liquid solution, a cream or a lotion.

4. The article of claim 1, wherein the composition is contained within an aerosol or non-aerosol spray device.

5. The article of claim 1, further comprising, packaged with said container and the instructions, a device for administering the composition for inhalation to the individual.

6. The article of claim 5, wherein the device is selected from the group consisting of a liquid pump device, a spray device, a nasal cannula, a face mask, and an adherent material for applying to skin of the individual.

7. The article of claim 1, further comprising, packaged with said container and the instructions, at least one of:
   a set of odorants for testing an individual's olfactory ability; and
   a set of serial dilutions of an odorant for testing olfactory threshold.

8. The article of claim 7, wherein the set of odorants for testing olfactory ability comprises a scratch-and-sniff identification test set of odorants.

9. An article, comprising, packaged together:
   a container of a composition consisting essentially of a jasmine odorant as a dominant odor in a carrier, the jasmine odorant at a suprathreshold but non-irritant concentration at about 25-55 decismel units and greater than an average normal threshold concentration of the jasmine odorant, the composition effective upon inhalation to improve an individual's score of a set number of frames in a bowling activity by a statistically significant amount compared to a control score determined by the individual's score of said set number of frames when the bowling activity is performed without inhalation of the composition; and
   instructions for administering the composition to an individual by inhalation during performance of the bowling activity and assessing the effectiveness of the composition.

10. An article, comprising, packaged together:
    a container of a composition comprising a mixture of odorants in a carrier, said mixture of odorants comprising a suprathreshold but non-irritant concentration of a jasmine odorant as a dominant odorant in combination with a less than suprathreshold concentration of one or more secondary odorants that complement and do not mask the jasmine odorant, the concentration of the jasmine odorant being at about 25-55 decismel units and greater than an average normal threshold concentration of the jasmine odorant, the composition effective upon inhalation to improve an individual's score of a set number of frames in a bowling activity by a statistically significant amount compared to the individual's score of said set number of frames when the bowling activity is performed without inhalation of the composition; and
    instructions for administering the composition to an individual by inhalation during performance of the bowling activity and assessing the effectiveness of the composition.

11. A method of enhancing performance of an individual in a scored bowling activity, comprising:
    having the individual inhale an effective amount of the composition of claim 1 while performing the bowling activity;
    recording the score of the individual; and
    assessing said score to determine effectiveness of inhaling the composition to enhance the performance of the individual in the bowling activity.

12. The method of claim 11, wherein the composition further comprises one or more secondary odorants that complement and do not mask the jasmine odorant, the secondary odorants at a less than suprathreshold concentration.

13. The method of claim 11, comprising applying the composition to skin beneath the nostrils of the individual.

14. The method of claim 13, comprising affixing an adherent material containing the composition onto skin beneath the nostrils of the individual.

15. The method of claim 11, wherein the composition is inhaled by the individual while performing the bowling activity.

16. The method of claim 11, wherein inhaling the composition improves the score of the individual by a statistically significant amount compared to a control score determined by the individual's score when said bowling activity is performed without inhalation of the composition.

17. The method of claim 16, further comprising having the individual perform the bowling activity in the absence of inhaling said odorant composition to provide the control score.

18. The method of claim 16, further comprising having the individual perform the bowling activity while inhaling a blank control to provide the control score.

19. An article, comprising, packaged together:
    a container of a composition comprising a jasmine odorant as a dominant odorant and one or more secondary odorants that complement and do not mask the jasmine odorant, the jasmine odorant at a suprathreshold and non-irritant concentration at about 25-55 decismel units and greater than an average normal threshold concentration of the jasmine odorant, and the secondary odorants at a less than suprathreshold concentration, the composition effective to improve a score of a set number of frames of an individual in a bowling activity, upon inhalation, by a statistically significant amount compared to the individual's score of said set number of frames upon performing the bowling activity without inhalation of the composition; and instructions for administering the composition to an individual by inhalation during performance of the bowling activity and assessing the effectiveness of the composition.

\* \* \* \* \*